United States Patent [19]

Grack

[11] Patent Number: 5,139,957

[45] Date of Patent: Aug. 18, 1992

[54] CHEMICAL INDICATOR THAT INCLUDES POTASSIUM DICHROMATE AND UREA AND METHOD OF USING THE SAME TO DETECT HYDROGEN PEROXIDE

[75] Inventor: Scott J. Grack, Erie, Pa.

[73] Assignee: American Sterilizer Company, Erie, Pa.

[21] Appl. No.: 528,671

[22] Filed: May 24, 1990

[51] Int. Cl.$^5$ ............................................. G01N 21/78
[52] U.S. Cl. ..................................... 436/135; 422/56; 436/1; 436/167; 436/169; 436/904
[58] Field of Search .................... 436/1, 135, 167, 169, 436/170, 904; 422/56–58, 61; 252/186.1

[56] References Cited

U.S. PATENT DOCUMENTS

| | | | |
|---|---|---|---|
| Re. 33,007 | 8/1989 | Bier | 422/28 X |
| 2,483,108 | 9/1949 | Silverman et al. | 422/56 |
| 3,183,173 | 5/1965 | Oakes . | |
| 3,654,180 | 4/1972 | Bauer . | |
| 3,704,096 | 11/1972 | Verses et al. . | |
| 4,033,264 | 7/1977 | Bolza et al. | 149/2 X |
| 4,128,399 | 12/1978 | Liotta et al. | 422/56 X |
| 4,169,123 | 9/1979 | Moore et al. | 422/29 |
| 4,169,124 | 9/1979 | Forstrom et al. | 422/33 |
| 4,181,540 | 1/1980 | Ahlf | 148/253 X |
| 4,195,057 | 3/1980 | Patel | 422/56 |
| 4,444,880 | 4/1984 | Tom | 422/56 X |
| 4,642,165 | 2/1987 | Bier | 422/28 X |
| 4,683,214 | 7/1987 | Angevine et al. | 502/64 X |
| 4,732,736 | 3/1988 | Kobayashi et al. | 422/56 |
| 4,734,360 | 3/1988 | Phillips | 435/25 |
| 5,002,844 | 3/1991 | Cheong et al. | 430/23 X |

FOREIGN PATENT DOCUMENTS 48-17118  5/1973  Japan .
277375  10/1970  U.S.S.R. .

OTHER PUBLICATIONS

Autoclave "Indicators", F. R. Elkins, M.P.S., The Pharmaceutical Journal, Jan. 11, 1947, pp. 31–32.
Compositions for the Detection of Hydrogen Peroxide, Research Disclosure, Aug. 1977, No. 16, 16034, pp. 19–24.
He, Chemical Abstracts, vol. 111, Abstract No. 111:213889u, 1989.

*Primary Examiner*—Robert J. Hill, Jr.
*Attorney, Agent, or Firm*—Kirkpatrick & Lockhart

[57] ABSTRACT

The present invention provides a chemical indicator for the detection of hydrogen peroxide. A composition containing an aqueous solution of potassium dichromate is applied to a porous substrate. The reaction between the dichromate and chromate ions present in solution and hydrogen peroxide is accompanied by a dramatic color change which is visible to the naked eye. The initial color of the potassium dichromate solution may be enhanced by adjusting the pH of the solution to be basic. The rate of reaction between the dichromate and chromate ions and the hydrogen peroxide may be increased by the addition of the humectant urea to the potassium dichromate solution.

17 Claims, No Drawings

CHEMICAL INDICATOR THAT INCLUDES POTASSIUM DICHROMATE AND UREA AND METHOD OF USING THE SAME TO DETECT HYDROGEN PEROXIDE

BACKGROUND OF THE INVENTION

1. Field of the Invention

This invention relates to chemical indicators, specifically indicators for the detection of vapor phase hydrogen peroxide.

2. Description of the Prior Art

U.S. Pat. No. 4,169,123 (Moore et al.) and U.S. Pat. No. 4,169,124 (Forstrom et al.) describe cold gaseous sterilization techniques using hydrogen peroxide gas as the sterilant. A primary concern to the operators of any sterilization equipment is whether or not the sterilizer functions properly to deliver the sterilant to the sterilization chamber. The need exists for an indicator which will detect the presence of hydrogen peroxide gas in the chamber and thus provide immediate verification that the sterilizer is operating correctly.

Test compositions and indicators for the detection of hydrogen peroxide in liquid solution are known in the art. U.S. Pat. No. 3,183,173 (Oakes) discloses a composition comprising an iodide salt, a metal catalyst and a high molecular weight polymer such as polyvinyl alcohol. Any hydrogen peroxide present in the test solution reacts with the iodide salt to produce free iodine. The iodine complexes with the polymer in the presence of the catalyst to produce a color change. U.S. Pat. No. 3,654,180 (Bauer) discloses an improvement on the indicator disclosed in the Oakes patent which uses α-naphthoflavone as the indicator dyestuff. Both the Oakes and Bauer indicator compositions rely on the complexing of free iodine with polymers in the presence of a metallic catalyst to produce a color change.

Soviet Union Patent No. 277,375 discloses an indicator strip which will detect the presence of hydrogen peroxide in the air. This strip is impregnated with a mixture of luminol, sodium carbonate and a copper catalyst. Luminol is a complex molecule which will emit light in the presence of hydrogen peroxide. A light producing reactant such as luminol does not undergo a permanent chemical transformation, reflected by a visible color change, upon exposure to hydrogen peroxide.

Color change as an indication that ozone sterilization is complete is known in the art. U.S. Pat. No. 3,704,096 (Verses et al.) teaches use of an aniline dye indicator strip and a cobaltous chloride indicator strip which are applied to an instrument to be sterilized in a transparent container. The strips react with ozone and humidity thereby undergoing color changes which verify that sufficient exposure occurred to effect sterilization. These indicator strips are unique to the detection of ozone and humidity and will not react with hydrogen peroxide.

Indicators which are used in ethylene oxide sterilization, another cold gaseous process, are incompatible with use in hydrogen peroxide vapor sterilization. Ethylene oxide indicators are based on a completely different chemical reaction than that which occurs during gaseous hydrogen peroxide sterilization. Thus, an indicator which detects ethylene oxide is not capable of detecting hydrogen peroxide vapor. Moreover, the concentration of hydrogen peroxide vapor sterilant is generally orders of magnitude lower than that of other gaseous sterilants. For example, the concentration of ethylene oxide required for sterilization is generally 600 mg/L compared to the maximum of 75 mg/L of hydrogen peroxide vapor disclosed in the Forstrom et al. patent referenced above. Thus, the indicators used in ethylene oxide sterilization would not respond to the low levels of hydrogen peroxide present during hydrogen peroxide gas sterilization, even if the chemical composition of the two sterilants were the same.

Similarly, the thermal indicators used in steam sterilization are based on a different chemical reaction than that of gaseous hydrogen peroxide sterilization and thus would not react with hydrogen peroxide. Steam sterilization is also a high temperature process (about 132° C.); the thermal indicators utilized therein will not function in hydrogen peroxide gas sterilization which is a cold process usually conducted at temperatures below 80° C.

It is an object of the present invention to provide an indicator for use in gaseous hydrogen peroxide sterilization systems. It is a further object of the present invention to provide such an indicator which will verify that vapor phase hydrogen peroxide sterilizers are operating properly by detecting the presence of hydrogen peroxide vapor in the sterilization chamber. It is a further object of this invention to provide an indicator which is simple to use and provides easily readable results.

SUMMARY OF THE INVENTION

The present invention provides a chemical indicator for the detection of hydrogen peroxide in both liquid and gaseous states. The indicator is comprised of a composition containing a predetermined amount of a potassium dichromate solution applied to a porous substrate. The potassium dichromate solution is of a concentration and an amount sufficient to detect exposure to a desired concentration of hydrogen peroxide at a desired temperature and pressure for a desired period of time. Detection of hydrogen peroxide is reflected by a color change visible to the naked eye in the porous substrate at a predetermined period of time.

The indicator of the present invention may be used in conjunction with hydrogen peroxide vapor sterilizers. The indicator allows the operator of this equipment to verify that the sterilizer is functioning properly to deliver hydrogen peroxide vapor to the sterilization chamber. The color change occurs when the potassium dichromate has completely reacted with hydrogen peroxide vapor present in the chamber. The concentration of hydrogen peroxide vapor, sterilization temperature and pressure and sterilization cycle time may be varied, along with the amount of potassium dichromate solution applied to the substrate to ensure that the color change will occur at a predetermined time. The midpoint of the sterilization cycle, which is believed to be the point at which sterility is achieved, may preferably be selected as the predetermined time.

In one embodiment of the present invention, a pH-modifying substance is added to the composition in an amount sufficient to make the composition basic. It has been found that this adjustment will brighten and stabilize the initial color of the composition and help to maintain that brightness after the composition has been applied to the substrate.

In an additional embodiment of the present invention, a predetermined amount of urea is added to the composition to attract water during the sterilization process. The urea is of an amount sufficient to increase the absorption rate of the hydrogen peroxide vapor by the substrate. The sterilant vapor is composed of both pure hydrogen peroxide vapor and water vapor. Urea, a humectant, attracts the water vapor portion of the sterilant vapor, thereby delivering the hydrogen peroxide vapor to the substrate at an increased rate, since the two are in a binary composition. The reaction between the potassium dichromate of the composition and the hydrogen peroxide vapor thus proceeds more quickly.

The advantages and benefits of the present invention will become apparent from the detailed description of the preferred embodiments hereinbelow.

DETAILED DESCRIPTION OF THE PREFERRED EMBODIMENTS

The present invention provides a chemical indicator which will detect the presence of hydrogen peroxide. It is anticipated that this indicator may be used for a variety of applications where it is desired to ascertain the presence of hydrogen peroxide. However, for purposes of describing the preferred embodiment of the invention and to aid in the understanding thereof, the indicator will be described in an embodiment suitable for use in hydrogen peroxide vapor sterilization processes.

Hydrogen peroxide vapor sterilization is a cold gaseous sterilization process which usually takes place at temperatures below 80° C., and preferably below about 44° C. A solution of hydrogen peroxide is either injected into a sterilization chamber where it is vaporized into water vapor and pure hydrogen peroxide vapor or is vaporized outside of the chamber and passed to it in the vapor form. The contaminated items within the chamber are surrounded by hydrogen peroxide vapor for an amount of time sufficient to effect sterilization.

The hydrogen peroxide vapor sterilant may be used in a variety of sterilization conditions which may be adjusted within various ranges, depending upon the intended use for the sterilizer and the type of goods which are to be sterilized. Concentration of hydrogen peroxide sterilant, the pressure within the chamber, the temperature at which the process is run, and the length of time of the sterilization cycle are sterilization conditions which may be varied as desired.

U.S. Pat. No. 4,169,124 (Forstrom et al.) sets forth possible ranges of operation for gaseous hydrogen peroxide sterilization processes. The concentration of hydrogen peroxide vapor may be within the range of 0.1 to 75 mg $H_2O_2$ vapor/L with a preferred range of 0.1 to 50 mg/L. The cycle time may range from 60 seconds to two hours. Temperature may vary from 20° C. to 80° C. Negative pressure may be applied, preferably greater than 15 inches of mercury. U.S. Pat. No. 4,169,123 (Moore et al.) discloses time periods up to 24 hours.

In the indicator of the present invention, a composition containing a potassium dichromate solution is applied to a porous substrate. Paper, such as ordinary typing paper or laboratory filter paper, is the preferred substrate. However, any substrate of a porosity sufficient to absorb hydrogen peroxide vapors will be a suitable substrate.

The potassium dichromate solution is of a concentration sufficient to detect the presence of hydrogen peroxide vapor under desired and preselected sterilization conditions. The detection of hydrogen peroxide vapor is reflected by a color change in the porous substrate which is visible to the naked eye. A potassium dichromate solution of a concentration within the range of 20-50 grams of potassium dichromate per liter of water has been found to be sufficient to detect hydrogen peroxide under the variety of sterilization conditions described above. A potassium dichromate solution having a concentration of 30 grams of potassium dichromate per liter of water is preferred.

It is believed that the color change reflected in the substrate is a result of a change in the oxidation number of the chromium ion portion of potassium dichromate. Potassium dichromate ionizes in water to form potassium cations and a mixture of dichromate anions and chromate anions. In aqueous solution, the dichromate anion is an orange-red color while the chromate anion is yellow. An aqueous solution containing both chromate and dichromate ions is characteristically yellow-orange. As the pH of the solution increases, dichromate anions are converted to chromate anions, making the solution a brighter yellow color. The majority of the chromium ions of both the dichromate and chromate anions have the oxidation number of +6. A minority of the chromium ions present are in the +3 oxidation state.

In the presence of hydrogen peroxide, the chromate and dichromate anions are oxidized and thereby undergo a chemical transformation resulting in a change in the oxidation number of the chromium ions. Upon exposure to an amount of hydrogen peroxide sufficient to completely react all of the chromate and dichromate ions in solution, the oxidation number of the chromium ion increases from +3 or +6 to +8. The change in oxidation number is reflected by a dramatic color change from yellow-orange to blue-violet visible to the naked eye.

Chromium ions with a +8 oxidation number are very unstable and do not remain in this state permanently. The instability is a result of the chromium ion's desire to gain electrons. Hydrogen peroxide within the sterilization chamber degrades into oxygen and water, a source for those electrons. The chromium ions are reduced to the preferred stable oxidation numbers of +3 and 0 by gaining electrons donated by the oxygen and water. As the chromium ions gain electrons to return to the stable state, the blue-violet color indicative of the +8 oxidation state gradually fades to the gray color indicative of the +3 and 0 oxidation states.

Upon application of the potassium dichromate solution to the substrate, the majority of chromium ions have a +6 oxidation number with a minority having a +3 oxidation number. The substrate exhibits the characteristic yellow-orange color. When hydrogen peroxide is delivered to the sterilization chamber under predetermined sterilization conditions, the substrate will absorb hydrogen peroxide vapors which completely react the chromate and dichromate ions, oxidizing the chromium to the higher oxidation state. Upon oxidation, the substrate will exhibit a dramatic color change from yellow-orange to blue-violet. When oxygen and water present in the chamber are absorbed by the substrate, the substrate will gradually fade to gray as the chromium is reduced to a preferred oxidation number and stable state.

The substrate is examined following completion of the sterilization cycle. If the substrate exhibits no yellow-orange color at all, all of the chromium ions have been oxidized, confirming that the sterilizer is operating correctly. As an indicator of operating performance, it does not matter whether the substrate is blue-violet or gray, as both indicate complete oxidation has occurred. The absence of the yellow-orange color is determinant of the presence of the desired amount of hydrogen peroxide. If there is any visible yellow-orange color, the sterilizer did not function in the intended manner.

The substrate is designed to undergo the color change at a predetermined time. The approximate midpoint of the sterilization cycle is generally regarded as the point at which sterility is achieved. Thus, it is a convenient reference point to select as the predetermined time for the color change to occur. It will be appreciated, however, that any point during the sterilization cycle may be selected as the predetermined time and that the amount of potassium dichromate can be adjusted to effect the color change at that time.

Since the color change is dependent upon the reaction of the potassium dichromate with hydrogen peroxide, the amount of potassium dichromate and the concentration may be varied to accommodate different conditions of the sterilization cycle which affect the delivery and amount of hydrogen peroxide.

In one embodiment of the present invention, a pH-modifying substance is added to the composition containing the potassium dichromate solution prior to application of the composition to the substrate. Without this addition, the initial color of the composition may slowly fade upon exposure to normal atmospheric conditions which can reduce the chromium ion. Despite this fading, the indicator would still function in the manner intended. However, by adjusting the pH to make the composition basic, the initial yellow-orange color is brightened and stabilized. The brighter initial color provides a sharper contrast between the initial yellow-orange and the subsequent blue-violet or gray which follows the reaction with hydrogen peroxide. The stability of the initial color gives the indicator a longer shelf-life so that it may be stored for longer periods of time before actual use. It has been found that a sodium hydroxide or potassium hydroxide solution is an effective pH-modifying substance with a 10% by volume potassium hydroxide solution preferred.

In an additional embodiment of this invention, urea is added to the composition prior to the application of the composition to the substrate. The urea is in an amount sufficient to increase the absorption rate of hydrogen peroxide vapor by the substrate. It has been found that about 175-200 g of urea per liter of prepared potassium dichromate solution is a sufficient amount for this purpose.

Urea is a humectant. A humectant is a substance which attracts and retains moisture to the material to which it is added. The sterilant vapor is composed of a binary composition of water vapor and hydrogen peroxide vapor. Urea attracts the water vapor to the substrate at an increased rate and consequently, simultaneously attracts the hydrogen peroxide vapor. Urea serves as a catalyst of the reaction by increasing the rate of absorption of hydrogen peroxide vapor by the substrate. Hence, the overall reaction between the peroxide and the dichromate proceeds more quickly.

While the oxidation by the hydrogen peroxide vapor occurs more quickly when urea is added to the indicator composition, so does the subsequent reduction of the unstable intermediate by the increased absorption of water vapor. The unstable intermediate exists for such a brief period of time that the blue-violet color normally exhibited is not visible. The reaction proceeds quickly from the initial yellow-orange to the gray of the stable and preferred chromium oxidation states of 0 and +3. The absence of any yellow-orange color on the substrate is still determinate of sufficient hydrogen peroxide exposure.

It will be appreciated by those skilled in the art that certain solvents, resins and varnishes, known commercially as ink formulations, may be added to the composition prior to its application to the substrate. Placing the components of the composition in an ink formulation increases the ease with which the composition may be applied to the substrate and increases the longevity of the substrate. Any suitable ink formulation which will not interfere with the reaction may be used, such as one obtained from ATI PyMaH Corporation in Hollywood Calif.

The following experiments were performed in a gaseous hydrogen peroxide sterilizer having an internal volume of approximately eight liters. The sterilant was thirty weight percent hydrogen peroxide liquid. The liquid sterilant was delivered to a vaporizer via a series of incremental injections where it was vaporized. The vapor was then passed to the sterilization chamber, consistent with the teachings of U.S. Pat. No. 4,642,165 (Bier) and U.S. Pat. No. RE 33,007 (Bier). The temperature remained constant at approximately 38° C., or 100° F., for all of the following experiments.

EXAMPLE 1

Three potassium dichromate solutions were prepared having concentrations of 10 g/L, 40 g/L and 100 g/L. Each solution was applied to strips of ordinary typing paper. Prior to exposure to hydrogen peroxide, the typing paper substrate was yellow in color. Upon exposure to hydrogen peroxide vapor in the gaseous hydrogen peroxide sterilizer described above for 16 minutes, the substrate changed color to violet. This color change was visible to the naked eye. It is believed that the violet color is indicative of the change in oxidation number of the chromium ion portion of the potassium dichromate due to complete oxidation by the hydrogen peroxide.

EXAMPLE 2

Five potassium dichromate solutions were prepared as follows:

(1) A 40 g/L solution was prepared by adding 2 grams of potassium dichromate to 50 ml of water. Five ml of 1N HCL were added to the potassium dichromate solution. The pH of the solution was measured to be 1.98.

(2) A 100 g/L solution was prepared by adding 5 grams of potassium dichromate to 50 ml of water. Five 5 ml of 1N HCL were added to the potassium dichromate solution. The pH of the solution was measured to be 1.98.

(3) A 40 g/L solution was prepared by adding 2 grams of potassium dichromate to 50 ml of water. The pH of the solution was adjusted to about 8.0 by the addition of a 10% by volume solution of sodium hydroxide.

(4) A 40 g/L solution was prepared by adding 2 grams of potassium dichromate to 50 ml of water. The pH of the solution was adjusted to about 12.5 by the addition of a 10% by volume solution of sodium hydroxide.

(5) A 100 g/L solution was prepared by adding 5 grams of potassium dichromate to 50 ml of water. The pH of the solution was adjusted to about 8.0 by the addition of a 10% by volume solution of sodium hydroxide.

Following application to typing paper substrates, but prior to exposure to hydrogen peroxide, it was visually observed that the substrates coated with the basic solutions (3), (4) and (5) were much brighter than the substrates coated with the acidic solutions (1) and (2). Solution 5, the most basic, provided the brightest yellow substrate. As the pH of the indicator composition increased, the brightness of the yellow color increased as well. Substrates coated with acidic solutions faded and did not maintain the bright initial yellow color.

Each substrate was exposed to hydrogen peroxide for ten minutes in the gaseous hydrogen peroxide sterilizer. All substrates turned violet following this exposure. Substrates were further examined after about 3.5 hours. The strips which were coated with solutions (2) and (5), having a potassium dichromate concentration of 100 g/L, had discolored. Discoloration of the substrate is caused by unreacted chromate and dichromate ions. Hence, at 100 g/L, the concentration of potassium dichromate was too high to completely react all of the dichromate and chromate ions with the hydrogen peroxide vapor.

The substrates coated with solutions (1), (3) and (4), having a potassium dichromate concentration of 40 g/L, retained the violet color indicative of the complete oxidation. The violet color of these substrates faded to the gray of the stable chromium oxidation state after 12 hours, indicating a complete reaction between the dichromate and chromate ions and the hydrogen peroxide vapor.

EXAMPLE 3

A number of solutions were prepared of various concentrations of potassium dichromate and potassium iodide. In all of the solutions, the pH was adjusted to 12.5 using a sufficient amount of 10% by volume potassium hydroxide solution. In all of the test solutions, the yellow color was brighter and more stable than that which had been observed in solutions where the pH had been similarly adjusted using a 10% by volume sodium hydroxide solution.

EXAMPLE 4

A composition comprising a 20 g/L potassium dichromate solution, an amount of 10% by volume potassium hydroxide solution sufficient to adjust the pH of the composition to about 12.5, a 20 g/L potassium iodide solution and 125 g/L of urea was applied to a substrate. The substrate was exposed to hydrogen peroxide vapor in a gaseous hydrogen peroxide sterilizer cycle of 16.5 minutes. At the approximate midpoint of the cycle, the substrate turned a blue/gray color and remained stable. The stable blue/gray color indicates that the dichromate and chromate ions completely reacted with the gaseous hydrogen peroxide.

EXAMPLE 5

A composition comprising a 20 g/L potassium dichromate solution, an amount of 10% by volume potassium hydroxide solution sufficient to adjust the pH of the composition to about 12.5, and 200 g/L of urea was applied to a substrate. The substrate was exposed to hydrogen peroxide vapor in a gaseous hydrogen peroxide sterilizer for 16 minutes. Following exposure, the substrate was completely gray, indicating a complete reaction of the dichromate and chromate ions with the hydrogen peroxide vapor.

In comparing the results of Example 4 and Example 5, it is observed that both compositions changed color, which indicates a complete reaction with hydrogen peroxide vapor. The presence or absence of potassium iodide did not effect the end result. Therefore, potassium iodide is not believed to participate in the reaction and is not a necessary component of the indicator composition.

It is also observed that the greater amount of urea used in Example 5 yielded a completely gray color rather than the mixed blue/gray of Example 4. The change to a single color is preferable in practical usage of the indicator for the ease afforded in the interpretation of sterilizer performance by the operator.

While the present invention has been described in connection with several examples and a proposed use in gaseous hydrogen peroxide sterilization technology, it will be understood that modifications and variations apparent to those of ordinary skill in the art are within the scope of the present invention.

What is claimed is:

1. A chemical indicator for the detection of hydrogen peroxide comprising a composition for application to a porous substrate, said composition comprising:
   (a) a predetermined amount of a potassium dichromate solution at a concentration sufficient to detect the presence of a desired concentration of hydrogen peroxide at a desired temperature and pressure for a desired period of time;
   (b) a pH-modifying substance in an amount sufficient to adjust the pH of said composition to a value between about 8 and about 12; and
   (c) a predetermined amount of urea, wherein said amount is sufficient to increase the absorption rate of hydrogen peroxide by said porous substrate.

2. A method for detecting hydrogen peroxide, the method comprising the steps of:
   (a) placing into a medium a chemical indicator having a desired color and being comprised of a solution of potassium dichromate applied to a substrate, wherein the concentration of potassium dichromate in the solution is sufficient to detect the presence of a desired concentration of hydrogen peroxide at a desired temperature and pressure, wherein the solution further comprises an amount of urea sufficient to increase the rate at which the substrate absorbs hydrogen peroxide; and then
   (b) ascertaining whether the chemical indicator changes color.

3. The method of claim 2 wherein the step of ascertaining whether the chemical indicator changes color comprises viewing the chemical indicator with the naked eye.

4. The method of claim 2 wherein the solution has a concentration of about 20 to about 50 grams potassium dichromate per liter solution.

5. The method of claim 2 wherein the concentration of the solution is about 30 grams potassium dichromate per liter solution.

6. The method of claim 2 wherein the solution further comprises a pH-modifying substance in an amount sufficient to make the solution basic.

7. The method of claim 6 wherein the pH-modifying substance is selected from the group consisting of potassium hydroxide and sodium hydroxide.

8. The method of claim 6 wherein the pH-modifying substance is a solution of 10% by volume sodium hydroxide.

9. The method of claim 2 wherein the substrate is a porous substrate.

10. The method of claim 9 wherein the porous substrate is selected from the group consisting of typing paper and laboratory filter paper.

11. The method of claim 2 wherein the amount of urea is about 175 to about 200 g of urea per liter of solution.

12. A method for detecting hydrogen peroxide, the method comprising the steps of:
   (a) placing into a medium a chemical indicator having a desired color and being comprised of a porous substrate to which has been applied a solution comprising about 20 to about 50 grams potassium dichromate per liter of solution, an amount of a pH-modifying substance sufficient to make the solution basic, and urea; and then
   (b) ascertaining whether the chemical indicator changes color.

13. The method of claim 12 wherein the step of ascertaining whether the chemical indicator changes color comprises viewing the chemical indicator with the naked eye.

14. A chemical indicator useful for detecting hydrogen peroxide, the chemical indicator comprising:
   (a) a porous substrate; and
   (b) a solution applied to the porous substrate, wherein the solution is comprised of potassium dichromate in a concentration sufficient to detect the presence of a desired amount of hydrogen peroxide at a desired temperature and pressure, a pH-modifying substance in an amount sufficient to make the pH of the solution basic, and urea.

15. The chemical indicator of claim 14 wherein the concentration of potassium dichromate in the solution is between about 20 to about 50 grams per liter of solution.

16. The chemical indicator of claim 14 wherein the concentration of the pH-modifying substance is such that the pH of the solution is about 8 to about 12.

17. The chemical indicator of claim 14 wherein the concentration of urea in the solution is between about 175 to about 200 grams per liter of solution.

* * * * *